United States Patent [19]

Middaugh et al.

[11] Patent Number: 5,348,941
[45] Date of Patent: Sep. 20, 1994

[54] STABILIZERS FOR FIBROBLAST GROWTH FACTORS

[75] Inventors: C. Russell Middaugh, Quakertown; Pei-Kuo Tsai, Blue Bell; David B. Volkin, Doylestown, all of Pa.

[73] Assignee: Merck & Co., Inc., Rahway, N.J.

[21] Appl. No.: 861,060

[22] Filed: Apr. 1, 1992

[51] Int. Cl.$^5$ .................. A61K 37/02; A61K 37/36
[52] U.S. Cl. .................. 514/12; 530/397; 530/399; 514/970; 514/21; 536/26.21; 536/26.23; 536/26.26
[58] Field of Search .............. 514/12, 21, 970; 530/397, 399; 536/26.21, 26.23, 26.26

[56] References Cited

U.S. PATENT DOCUMENTS

| | | | |
|---|---|---|---|
| 4,785,079 | 11/1988 | Gospodarowicz et al. | 530/413 |
| 4,868,113 | 9/1989 | Jaye et al. | 435/70 |
| 4,956,455 | 9/1990 | Esch et al. | 530/839 |
| 5,130,418 | 7/1992 | Thompson | 530/399 |
| 5,175,147 | 12/1992 | Falkman | 514/12 |

FOREIGN PATENT DOCUMENTS

| | | |
|---|---|---|
| 259953 | 7/1987 | European Pat. Off. |
| 267015 | 11/1987 | European Pat. Off. |
| 312208 | 9/1988 | European Pat. Off. |
| 319052 | 10/1988 | European Pat. Off. |
| 345680 | 6/1989 | European Pat. Off. |
| 392605 | 4/1990 | European Pat. Off. |
| 406856 | 7/1990 | European Pat. Off. |
| 408146 | 7/1990 | European Pat. Off. |
| WO90/03797 | 4/1990 | PCT Int'l Appl. |
| WO87/01728 | 3/1987 | World Int. Prop. O. |

OTHER PUBLICATIONS

Guranowski, et al., *Chemical Abstracts*, 107, 1987, Abst No. 19872k.
Tarusono, et al., *Chemical Abstracts*, 105, 1986, Abst. No. 227204e.
Feldhaus, et al., *Chemical Abstracts*, 83, 1975, Abst. No. 159849u.
Foresch et al., Ann. Rev. Physiol. 47: 443–467, 1985.
Sharath et al., Immunopharm. 9: 73–80, 1985.
Ortega et al., J. Biol. Chem. 266: 5842–5846, 1991.
Gimenez-Gallego et al., Biochem Biophys. Res. Comm. 138: 611–617, 1986.
Rosengart et al., Biochem Biophys. Res. Comm. 152: 432–440, 1988.
Baird & Bohlen, Growth Factors 1: 369–418, 1990.
Klagsburn, Cur Opin Cell Biol. 2: 857–863, 1990.
Brown et al., J. Exp. Med. 163: 1319–1324, 1986.
Thomas et al., Proc. Natl. Acad. Sci. USA 82: 6409–6413, 1985.
Gospodarowicz et al., Endocrine Reviews 8: 95–113, 1987.
Marzella et al., Wounds: A Compendium of Clinical Research & Practice 2: 135–147, 1990.
Raake et al., Thrombosis R. 56: 719–730, 1989.
Riddles, et al., Meth Enzymol. 9: 49–60, 1983.
Gospodarowicz & Cheng, J. Cell Physiol. 128: 475–484, 1986.
Sakaguchi et al., J. Biol. Chem. 266: 7270–7278, 1991.
Sakesla et al., J. Cell Biol. 107: 743–751, 1988.
Mueller et al., J. Cell Physiol. 140: 439–448, 1989.

(List continued on next page.)

*Primary Examiner*—F. T. Moezie
*Attorney, Agent, or Firm*—John W. Wallen, III; Jack L. Tribble; Paul D. Matukaitis

[57] ABSTRACT

Medicinal compositions containing fibroblast growth factor are stabilized against loss of biological activity by including in said composition a stabilizing amount of phytic add, phosvitin, phosphate buffer, $(NH_4)_6P_4O_{13}$, $Na_5P_3O_{10}$, $Na_4P_2O_7$ and $Na_3P_3O_9$, adenosine tetra, tri, di and mono phosphate and related diadenosine compounds plus other single and multi-phosphorylated mono and di-nucleotides, poly-aspartic acid, poly-adenylic-guanylic add and related compounds, double stranded deoxyribonucleic add, single stranded deoxyfibonucleic acid and poly-glutamic acid. Medicinal compositions for topical use are combined with a viscous excipient such as a water soluble polysaccharide with said combination with a second stabilizier.

1 Claim, 10 Drawing Sheets

OTHER PUBLICATIONS

Sommer & Rifkin, J. Cell Physiol. 138: 215–220, 1989.
Squires et al., J. Biol. Chem. 263: 16297–16302, 1988.
Rice & Linhardt, Carbo. Res. 190: 219–233, 1989.
Yayon et al., Cell 64: 841–848, 1991.
Vlodavsky et al., J. Cell. Biochem. 45: 167–176, 1991.
Linemeyer et al., Growth Factors 3: 287–298, 1990.
Jackson et al., Physiological Reviews 71: 481–539, 1991.
Eriksson et al., Proc. Natl. Acad. Sci. USA 88: 3441–3445, 1991.
Zhu et al., Science 251: 90–93, 1991.
Zhang et al., Proc. Natl. Acad. Scie. USA 88: 3446–3450, 1991.
Lane & Lindahl, Heparin 25–49, 1989.
Burgess & Maciag, Annu. Rev. Biochem. 58: 575–606, 1989.
Gospodarowicz, Clin. Orth. Relat. R. 257:231–248, 1990.
Hakim & Linhardt, Electroph. 11: 23–28, 1990.

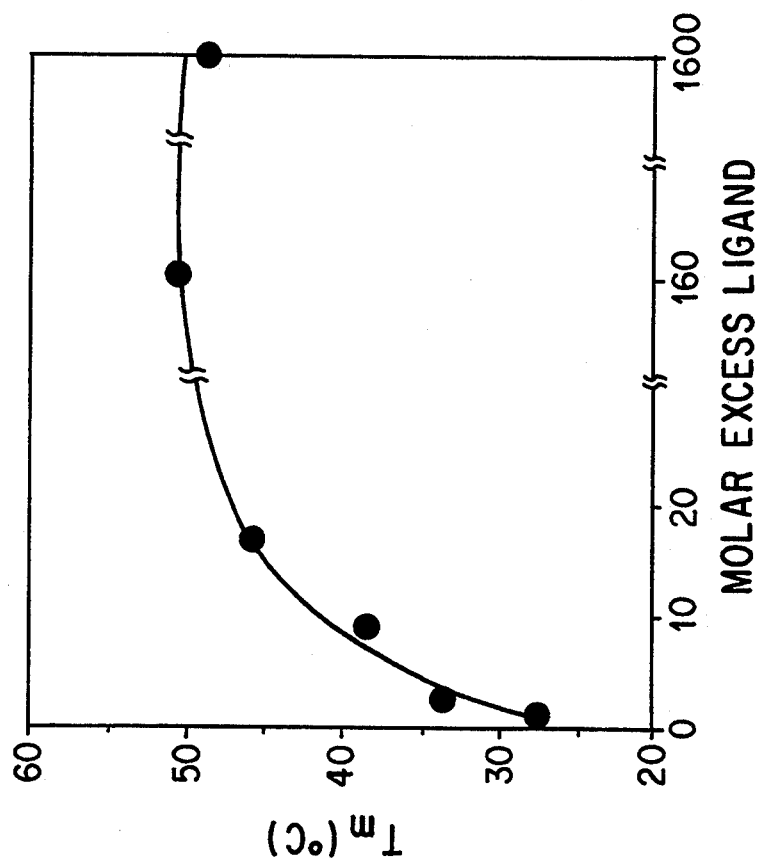
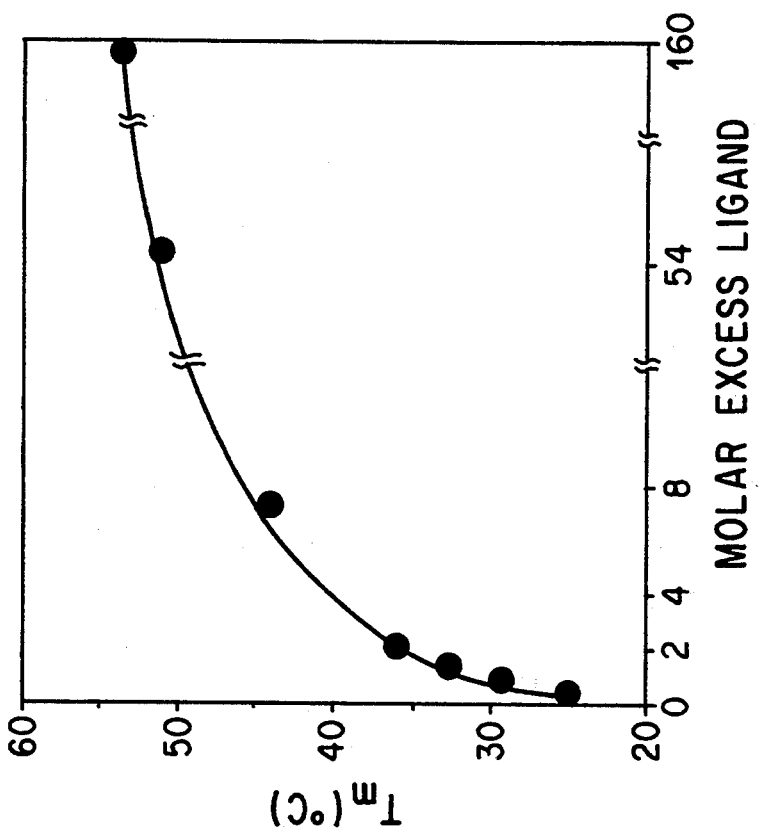
FIG. 9B
FIG. 9A

STABILIZERS FOR FIBROBLAST GROWTH FACTORS

BACKGROUND OF THE INVENTION

Fibroblast growth factors (FGF) are angiogenic polypeptide mitogens with mitogenic activity for a wide variety of cell types, see reviews: Gospodarowicz et al., Endocrine Reviews 8:95-113 (1987); Burgess and Maciag, Annu. Rev. Biochem. 58:575-606 (1989); Gospodarowicz, Clin. Orthop. Relat. R. 257:231-248 (1990); Baird and Bohlen, In Peptide Growth Factors and Their Receptors 1, pp. 369-418, Springer-Verlag, Berlin (1990). Fibroblast growth factors are classified either as acidic fibroblast growth factor (aFGF) with a molecular mass of about 15.9 kDa or basic fibroblast growth factor (bFGF) with a molecular mass of about 16.3 kDa. A distinctive feature of FGF is a dependence on the presence of polyanions such as heparin for in vitro biological activity and structural integrity: Gospodarowicz et al., Endocrine Reviews 8: 95-113 (1987); Burgess and Maciag, Annu. Rev. Biochem. 58: 575-606 (1989); Gospodarowicz, Clin. Orthop. Relat. R. 257: 231-248 (1990); Baird and Bohlen, In Peptide Growth Factors and Their Receptors 1, pp. 369-418, Springer-Verlag, Berlin (1990). Like a wide variety of plasma proteins, FGF interacts strongly with heparin and is often isolated by affinity chromatography using heparin as a ligand with different salt concentration required for elution: aFGF, 1.0 M; bFGF, 1.6 M. One striking manifestation of the FGF/heparin interaction is protection of the growth factor from proteolytic, acidic and thermal inactivation: Gospodarowicz and Cheng, J. Cell Physiol. 128: 475-484 (1986); Rosenbart et al., Biochem. Biophys. Res. Comm. 152:432-440 (1988); Sakesla et itl., J. Cell Biol. 107: 743-751 (1988), Mueller et al., J. Cell Physiol. 140:439-448 (1989); Sommer and Rifkin J. Cell Physiol. 138:215-220 (1989). In vivo, the protein is often found associated extracellularly with heparan sulfate proteoglycans which presumably provide a natural stabilizing environment: Klagsbum, Cur. Opin. Cell Biol. 2:857-863 (1990); Sakaguchi et al., J. Biol. Chem. 266:7270-7278 (1991); Yayon et al., Cell 64: 841-848 (1991). It has been postulated that release of FGF from the extracellular matrix by heparanases is used to regulate the availability of active growth factor, Vlodavsky, et al., J. Cell. Biochem. 45:167-176 (1991). This may also explain the lack of a conventional signal sequence in the protein, Gospodarowicz et al., Endocrine Reviews 8:95-113 (1987); Burgess and Maciag, Annu. Rev. Biochem. 58:575-606 (1989); Gospodarowicz, Clin. Orthop. Relat. R. 257:231-248 (1990); Baird and Bohlen, In Peptide Growth Factors and Their Receptors 1, pp. 369-418, Springer-Verlag, Berlin (1990).

OBJECTS OF THE INVENTION

It is, accordingly, an objective of the present invention to provide unique stabilizers which stabilize both aFGF and bFGF against both thermal and chemical degradation. A further object is to provide phosphorylated compounds as FGF stabilizers. Another object is to provide linear and cyclic polyphosphate, including phosphate buffer ions, as FGF stabilizers. Another object is to provide phosphorylated nucleotide aFGF stabilizers. A further object is to provide polyaspartic acid, poly-adenylic-guanylic add and related compounds, double stranded deoxyribonucleic acid, single stranded deoxyribonucleic add and poly-glutamic acid as FGF stabilizers. A further object is to provide stabilized aFGF or bFGF by combining the FGF with phosphorylated compounds. Another object is to provide stabilized aFGF by combining aFGF with linear and cyclic polyphosphates. Another object is to provide stabilized aFGF by combining aFGF with poly-aspartic acid, poly-adenylic-guanylic add and related compounds, double stranded deoxyribonucleic acid, single stranded deoxyribonucleic acid and poly-glutamic add. A further object is to provide a combination of excipients that when mixed with aFGF and a stabilizer results in a viscous formulation stable at room temperature and exhibits full mitogenic activity in cell culture and demonstrates biological activity in vivo to accelerate wound healing or tissue repair. Another object is to provide a viscous film of aFGF on a non-horizontal surface which will retain bioactivity following drying of the film.

SUMMARY OF THE INVENTION

Medicinal compositions containing acidic fibroblast growth factor are stabilized against loss of biological activity by including in said composition a stabilizing amount of phytic add, phosvitin, phosphate buffer, $(NH_4)_6P_4O_{13}$, $Na_5P_3O_{10}$, $Na_4P_2O_7$ and $Na_3P_3O_9$), adenosine tetra, tri, di and mono phosphate and related diadenosine compounds plus other phosphorylated nucleotides, poly-aspartic add, poly-adenylic-guanylic add and related compounds, double stranded deoxyribonucleic add, single stranded deoxyribonucleic acid and poly-glutamic acid. Medicinal compositions for topical use are combined with a viscous excipient such as a water soluble polysaccharide with said combination with a second stabilizier.

DETAILED DESCRIPTION OF THE INVENTION

Figure 1:
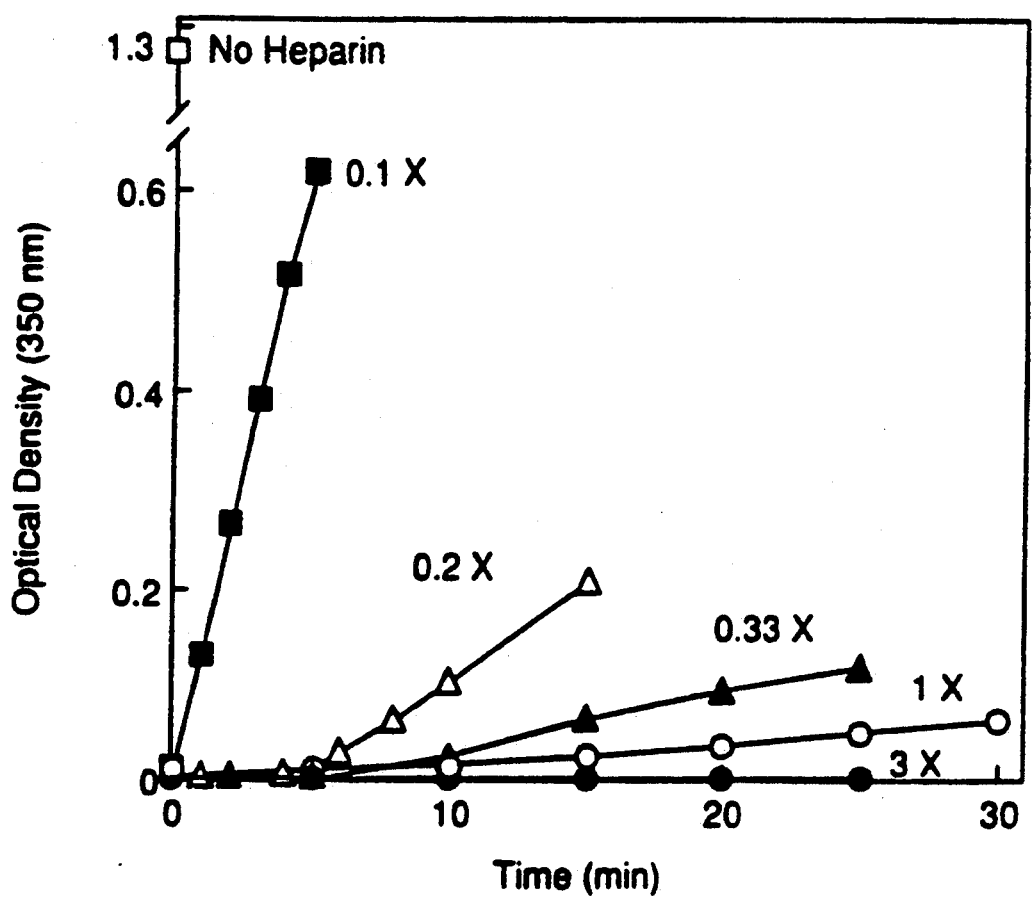
FIG. 1. Time course of the heat-induced aggregation of acidic aFGF at 55° C. as monitored by turbidity measurements at 350 nm in the presence of varying amounts of heparin.

The present invention relates to stable topical or parenteral formulations of human acidic fibroblast growth factor (aFGF). The invention further relates to a very diversified group of unique aFGF stabilizers and compositions containing said stabilizers combined with aFGF. The stabilized aFGF combinations are useful for wound healing and tissue repair. The embodiment of this invention results in a stable formulation that exhibits full mitogenic activity in cell culture and demonstrates full biological activity in vivo to accelerate wound healing.

Human acidic fibroblast growth factor exists in various microheterogeneous forms which are isolated from various tissue sources. Microheterogeneous forms as used herein refer to a single gene product, that is a protein produced from a single gene unit of DNA, which is structurally modified following translation. These structural modifications, however, do not result in any significant alterations of biological activity of the polypeptide. Biological activity and biologically active are used interchangeably and are herein defined as the ability of native and recombinant aFGF to stimulate DNA synthesis in quiescent BALB/c 3T3 fibroblasts or to stimulate any of the cell types described in the art or to carry out any of the functions described in the art, most specifically topical wound healing or tissue repair. The modifications may take place either in vivo or during the isolation and purification process. In vivo modification results in, but is not limited to, acetylation at the N-terminus, proteolysis, glycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the polypeptide at specific locations within the amino acid sequence. Similar modifications can occur during the purification process which also results in the production of microheterogeneous forms. The most common modification occurring during purification is proteolysis which is generally held to a minimum by the use of protease inhibitors. Under most conditions a mixture of microheterogeneous forms are present following purification of native aFGF. Native aFGF refers to aFGF isolated and purified from tissues or cells that contain aFGF.

Native human aFGF exists in the following microheterogeneous forms. The most preferred microheterogeneous forms of human aFGF include a 154 amino acid form, a 140 amino acid form and a 139 amino acid form. The amino acid sequence for the human 139, 140 and 154 amino acid forms of aFGF are described in U.S. Patent No. 4,868,113 and European Patent Application, Publication No. 259,953. The various forms of human aFGF can be synthesized by either recombinant biotechnological procedures as described in European Patent Application, Publication No. 259,953 or purified from human tissue as described by Gimenez-Gallego et al., Blochem. Biophys. Res. Commun. 138:611–617 (1986). These procedures can also be used to produce any microheterogeneous form of aFGF which is active as a wound healing agent. The recombinant derived, 140 amino acid form is the preferred form of aFGF. The preferred embodiment of this invention will include recombinant human aFGF produced in microbial cells and will have attached to the first amino acid residue of the amino terminus a methionine residue (MetHaFGF). Thus, the most preferred form of human aFGF will be a 141 amino acid form. The genes and methods of preparing the aFGF are well known in the art, see above references.

Native human bFGF also may exist in microheterogeneous forms. Basic FGF can be obtained by the methods described in U.S. Pat. Nos. 4,785,079 and 4,956,455. The various forms of human bFGF can be synthesized by either recombinant biotechnological procedures as described in Patent Cooperation Treaty/U.S. No. 86/01879 or by Squires et al., J. Biol. Chem. 263:16297–16302 (1988). These procedures can also be used to produce any microheterogeneous form of bFGF which is active as a wound healing agent. The preferred embodiment of this invention will include recombinant human bFGF produced in microbial cells and will have attached to the first amino acid residue of the amio terminus a methionine residue (MetHbFGF).

It is intended that the scope of the invention will include both aFGF and bFGF and either growth factor can be stabilized by the stabilizers disclosed herein. Moreover, it is intended that when aFGF is used hereinafter, bFGF is also intended and in almost all situations bFGF can be substituted for aFGF.

The concentration of aFGF in the following formulations, for topical use, is usually within the range of from about 0.1 ng/ml to about 1500 $\mu$g/ml of aqueous formulation (this includes either the initial aqueous formulation or a formulation that has been reconstituted after dehydration).. The preferred concentration of FGF for topical formulation is from about 25 $\mu$g to about 800 $\mu$g/ml. The most preferred concentration of FGF for topical formulations is from about 50 $\mu$g/ml to about 250 $\mu$g/ml. The concentration for parenteral use is usually within the range of from about 1 ng/ml to about 1500 $\mu$g/ml of the aqueous formulation (this includes either the initial aqueous formulation of a formulation that has been reconstituted after dehydration. The most preferred concentration of FGF for parenteral formulations is from about 25 $\mu$g to about 800 $\mu$g.

Several alternative final isolation steps are employed from different batches of cells, all resulting in aFGF of similar purity (>99%), specific mitogenic activity, and spectroscopic properties, European Patent Application, Publication No. 408,146. Final sample purity is assessed by SDS/PAGE using silver staining. Protein concentration is determined spectrophotometrically using an extinction coefficient of $E_{280}^{0.1\%} = 1.2$.

Homogeneously pure human aFGF is not chemically and/or conformationally stable or biologically active without being stabilized. Stabilization as used herein refers to the addition of chemicals capable of interacting directly with aFGF to maintain a stable and biologically active molecule and chemicals which can maintain stability without direct interaction with aFGF. The present invention includes a formulation in which at least one or both types of stabilizing chemicals is present.

Heparin was purchased from Hepar ®, low molecular weight heparin from Calbiochem, and the enzymatically prepared heparin fragments were prepared by procedures disclosed in the following references: Rice and Linhardt; Carbo. Res. 190:219–233 (1989), Hakim and Linhardt, Eletroph. 11: 23–28 (1990), Sharath et al., Immunopharm. 9:73–80 (1985). Sulfated lactobionic acid amide was prepared by the method of Raake et al, Thrombosis. R. 56:719–730 (1989). The isomeric purity of the di, tetra and hexasaccharides of heparin is >95% while the octa and deca fragments were mixtures. Chemical structures of di, tetra and hexa heparin fragments are as follows:

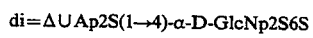

di=ΔUAp2S(1→4)-α-D-GlcNp2S6S

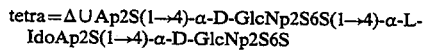

tetra=ΔUAp2S(1→4)-α-D-GlcNp2S6S(1→4)-α-L-IdoAp2S(1→4)-α-D-GlcNp2S6S

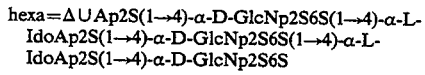

hexa=ΔUAp2S(1→4)-α-D-GlcNp2S6S(1→4)-α-L-IdoAp2S(1→4)-α-D-GlcNp2S6S(1→4)-α-L-IdoAp2S(1→4)-α-D-GlcNp2S6S (Where ΔUAp is 4-deoxy-α-L-threo-hex-4-enopyranosyl uronic acid, p is pyranose, GlcA and IdoA are glucuronic and iduronic acid, respectively, and S is sulfate.)

Sulfated and nonsulfated γ- and β-cyclodextrins were obtained from American Maize. Fucoidan fractions 1 and 2 (precipitates from increasing amounts of organic solvent) were purchased from Kelco. All other sulfated polysaccharides, polyanions and other compounds are purchased from Sigma. Other reagents are purchased commercially and of the highest grade available.

Stabilization of aFGF can be determined by several independent methods including turbidity measurements, spectroscopic techniques, maintenance of protein mass, mitogenic activity and copper catalyzed oxidation. Since acidic fibroblast growth factor is unstable at physiological temperatures (undergoing large structural changes, including aggregation, which results in a loss of mitogenic and wound healing activity), human aFGF stability can be monitored by evaluating the turbidity of the pharmaceutical composition by following the kinetics of temperature induced aggregation of unfolded protein.

The kinetics of protein aggregation (stabilization) are monitored by the degree of light scattering at about $OD_{350}$ nm using a Perkin Elmer Lambda 6 UV-visible spectrophotometer equipped with a six-cuvette holder. Temperature is controlled by circulating a water/ethylene glycol solution through the cell holder. About 0.9 ml of a PBS solution (6 mM sodium phosphate, 120 mM NaCl, pH 7.2) was placed into a cuvette and incubated at the appropriate temperature within the spectrophotometer. Once equilibrated, 100 μl of a 1 mg/ml aFGF solution containing the appropriate amount of ligand (stabilizer) is added to the cuvette and mixed manually by inversion. The change in optical density at 350 nm over time is continuously monitored. A dead time of 30s was present due to the mixing of the six samples in each experiment. Aggregate formation was irreversible.

Circular Dichroism (CD) spectra are measured with an AVIV 62 DS spectropolarimeter. Samples of aFGF at about 100 μg/ml in a PBS buffer (6 mM sodium phosphate, 120 mM NaCl, pH 7.2) containing various ligands are placed into 1 mm pathlength cells and the cell temperature is controlled by circulating a water/ethylene glycol mixture through the cell holder. Thermal denaturation is carried out under computer control by increasing the temperature of the water bath in 2° C. increments, followed by a two-minute equilibration period at each temperature to allow the sample to reach thermal equilibrium. Reproducibility of the midpoint of these temperature melting curves ($T_m$) is ±2° C.

Fluorescence spectra are obtained with a Spex Fluorolog-2 spectrofluorometer using a 1 mm pathlength cuvette. Band passes from 1–2 nm are employed with sample absorptivities maintained below 0.1 at 280 nm. The temperature is controlled either manually or automatically as described above. Reproducibility of thermal denaturation temperatures ($T_m$) is ± 2° C.

Size exclusion high performance liquid chromatography (SEC-HPLC) is also used to monitor human aFGF stability by determining the per cent protein mass of a sample. This technique incorporates a phosphate-cesium chloride mobile phase with detection at about 215 nm. Test samples are diluted to about one to ten (1/10) in mobile phase and the aFGF peak areas are compared to a aFGF standard of known concentration.

Biological activity of the formulation of the instant invention is determined by a modification of the fibroblast mitogenic assay as described by Linemeyer et al. in European Patent Application, Publication No. 259,953. BALB/c 3T3 A31 fibroblasts (American Type Culture Collection) are plated at about $3 \times 10^5$ cells per 32 $cm^2$ wells in culture media containing about 10% heat-inactivated calf serum and incubated in about 7% $CO_2$ (pH 7.35±0.05). The cells become fully quiescent by replacing the media with serum free media at about 6, about 24 hours and about 48 hours later. At about 53 hours after plating samples of the various formulations are added and about 0.12 μg of dexamethasone are added. At about 65 hours each well is supplemented with about 0.4 μCi of [methyl-$^3$H]-thymidine (20 Ci/mmole, Dupont) and 0.6 μg of unlabeled thymidine (Sigma), and at 80 hours the cells are processed for determination of radiolabel incorporation into DNA. Each dose-response point is the average of at least quadruplicate determinations. Other cell types such vascular endothelial cells and corneal endothelial cells can be employed to determine in vitro mitogenicity. The procedures are described in detail by Thomas et al., Proc. Natl. Acad. Sci. USA 82:6409–6431 (1985).

In vitro mitogenicity is a direct correlate of cell division which can result in tissue growth. It is well known in growth factor research that potent in vitro mitogens are also effective as in vivo growth stimulators. Epidermal growth factor (EGF) is a promoter of keratinocyte growth in vitro and also accelerates epidermal regeneration in vivo, Brown et al., J. Exp. Meal. 163: 1319–1324 (1986). Insulin-like growth factors also stimulate division and growth of many different cultured cells and also stimulate growth in vivo, Foresch et al., Ann. Rev. Physiol. 47: 443–467 (1985). Acidic fibroblast growth factor stimulates various cells to divide in vitro, such as fibroblasts, vascular and corneal endothelial cells, as described above, chondrocytes, osteoblasts, myeloblasts, smooth muscle, glial cells and neuroblasts, European Patent Application, Publication No. 319,052. Thomas et al., Proc. Natl. Acad. Sci. USA 82:6409–6413 (1985), has shown a direct correlation between in vitro mitogenic stimulation and an angiogenic response of chicken egg chorioallantoic membrane which is an example of tissue growth.

Clotting times are monitored by either a one-stage plasma prothrombin time assay (PT assay) or an activated partial thromboplastin time assay (aPTT) using an automated optical detection system (coag-a-Mate®-XC) by General Diagnostics. Clotting times are measured in the presence of varying amounts of heparin (0–50 μg heparin/ml plasma) to generate a standard curve and clotting times of other compounds (at equal wt. amounts) are obtained relative to these standardized values.

Copper-catalyzed oxidation of aFGF is carried out in the following manner. Acidic FGF (about 80 μg/ml) is incubated in a 20 mM Tris, 0.15M potassium chloride, pH 8 solution containing about 20 μM cuptic chloride for varying periods of time at room temperature. The reaction was terminated by the addition of 100 mM EDTA in the same buffer. A solution of about 0.7 ml of 0.25M Tris (about pH 8) containing about 2 mM EDTA and about 7 M GuHC1 is then added followed by about 35 μl of 4 mg/ml of DTNB (Sigma). Samples were incubated for 30 minutes, filtered through a 0.22 micron filter and the optical density measured at about 412 nm to determine sulfhydryl content, Riddles et al., Meth. Enzymol. 9:49–60 (1983). Relative standard deviation of the obtained values during time course experiments is 12%.

Differential scanning calofimetry studies employed a Hart 7708 calorimeter and protein concentration of about 1 mg/ml at a scan rate of about 60° C./hr.

The in vivo animal wound healing model employs genetically diabetic c57GBL/Ks- db+/db+ female mice. The assay follows that described by Marsella et al., Wounds: A Compendium of Clinical Research and Practice, 2, (4) July/August 1990, p. 135–147, except that a single 2 cm² full thickness wound is used instead of the two 6 mm biopsy wounds described by Marsella. Another difference is that the wounds are covered with a polyurethane dressing. Addic FGF is applied to wounds on days 0, 3 and 7. Matching placebo formulations are used in a second group of animals. Dressings are changed every three to four days, at which time wound perimeters are traced for assessment of healing. Comparison of healing rate va. a placebo control is made and evaluated for statistical significance at the 90% healed stage.

The processes as described above are used to identify the human aFGF stabilizers of the present invention. The turbidity assay is a rapid screening technique used to examine the ability of a wide variety of excipients and ligands to stabilize aFGF. The most promising compounds are then examined by both detailed biophysical studies including, but not limited to, circular dichroism, differential scanning colormetry and fluorescence spectroscopy, and also real-time stability studies (up to 3 months). Finally, compounds are used to stabilize human aFGF for the testing of efficacy in an in vivo animal wound healing model.

Stabilizers of human aFGF can be separated into essentially two major categories: specific ligands that directly interact with and stabilize aFGF and nonspecific excipients that either bind weakly to aFGF or exert their stabilizing effect through perturbation of solvent structure. The stabilizers of the present invention are specific ligands which are polyanions and can be further grouped as heparin-like molecules, sulfated polysaccharides, small sulfated molecules, phosphorylated polyanions and other highly charged polyanions. Heparin-like compounds include, but are not limited to, chondroitin sulfate A, chondroitin sulfate B, chondroitin sulfate C, enzymatically and synthetically prepared heparin fragments consisting of di, tetra, hexa, octa and decasaccharides. Sulfated polysaccharides include, but are not limited to, low molecular weight heparin, sulodexide, dextran sulfate, sulfated lactobionic acid amide and sulfated bis-aldonic acid amide, sucrose octasulfate, fucoidan 1, fucoidan 2, sulfated β-cyclodextrin, sulfated γ-cyclodextrin and pentosan polysulfate. Small sulfated compounds include, but are not limited to, inositol hexasulfate, tiron, ammonium sulfate and sodium sulfate. Phosphorylated polyanions include, but are not limited to, compounds such as phosphorylated inositol compounds (especially phytic acid), phosvitin, phosphate buffer, linear and cyclic pollyphosphates (such as $(NH_4)_6P_4O_{13}$, $Na_5P_3O_{10}$, $Na_4P_2O_7$ and $Na_3P_3O_9$), phosphorylated nucleotides such as adenosine tetra, tri, di and mono phosphate and related diadenosine compounds ($Ap_nA$, $n=1-6$) plus other single and multiple phosphorylated mono and di-nucleotides. Other highly charged polyanions include, but are not limited to, polyaspartic acid, poly-adenylic-guanylic acid and related compounds, double stranded deoxyribonucleic acid, single stranded deoxyribonucleic acid and polyglutamic acid.

Stability of the aFGF formulation of this invention is determined by real time stabilization studies in which sterile samples of the formulation are stored at specific temperatures for periods of time up to 3 months. Accelerated stabilization determinations, as described above, are made by maintaining the formulation of this invention at temperatures between about 400° C. and about 550° C.

Topical formulations of aFGF may require relative long derreal contact dosing and thus require a formulation which prevents loss of the drug due to run off. To achieve these ends aFGF combined with a aFGF stabilizer are combined with a polymer which forms a stable viscous solution even after a freeze/thaw cycle at +70° C. An acceptable polymer is one which dissolves easily and forms a viscous solution in both water and phosphate buffered saline. The upper concentration limit is about 1.5%. The solution (without aFGF) must be able to withstand autoclave sterilization without apparent changes in the inherent properties. The final formulation containing aFGF must withstand freeze-thaw cycles without any significant change in viscosity. Indeed, the ideal excipient will be one which results in an elastic moisture-retaining film that remains on the wound for extended periods of time and releases the aFGF into the wound environment.

The viscous excipients or polymers of the present invention are water soluble polymers such as xanthan gum, alignates or cellulose derivatives such as alkyl celluloses, hydroxyalkyl celluloses and alkylhydroxyalkyl celluloses. Examples of viscous excipients include methyl cellulose, hydroxyethyl cellulose, carboxymethyl cellulose, hydroxypropyl methylcellulose with hydroxyethyl cellulose (HEC) being preferred. The concentration of the preferred excipient, HEC, will range form about 0.25% to about 2% on a weight/volume basis with a concentration of about 0.75% to about 1.25% being the most preferred.

Formulations containing aFGF in combination with an aFGF stabilizer and HEC may not be completely stable at temperatures above about 4° C. for extended periods of time. Indeed, aFGF plus heparin and HEC becomes unstable at room temperature for extended periods of time and loses both in vitro and in vivo activity following extended storage. The addition of HEC may cause a destabilization of the aFGF-heparin combination at temperatures above about 4° C. which results in the loss of biological activity. The aFGF-stabilizer-HEC combination must be further stabilized by compounds that bind trace metal ions. This is extremely important because aFGF contains three free cysteine residues within the polypeptide chain. Thiol groups can be oxidized spontaneously by atmospheric oxygen. The process is catalyzed by trace metal ions, especially copper and iron. Free metal ions must be sequestered and unavailable to catalyze oxidation to maintain stabilized aFGF. One way of blocking the metal ions is to add a chelating agent which can bind the free metal ions. Consequently, an integral part of the present invention is the addition of a chelating agent to the combination of aFGF, stabilizer and HEC to maintain the ultimate stability of the combination. The chelating agents may include, but are not limited to, ethylenediaminetetraacetic add (EDTA) or EDTA salts and ethyleneglycolbis($\beta$-aminoethyl ether) N,N,N', N'-tetraacetic add (EGTA) and EGTA salts along with related compounds. The salts include, but are not limited to, calciumdisodium, disodium, tetrasodium, trisodium. The preferred chelater is EDTA at a concentration ranging from about 0.05 mM to about 10 mM, with the most preferred concentrations being from about 0.075 mM to about 0.5 mM. Weaker chelating agents such as citrate or histidine are not as effective as EDTA or EGTA and the respective salts in stabilizing the aFGF-stabilizer-HEC combination.

Stabilized, biologically active aFGF is useful in promoting the repair or healing of, but not limited to, soft tissue wounds resulting from burns, cuts or lacerations, and cutaneous ulcerations along with musculo-skeletal wounds such as bone fractures, ligament and tendon tears, and inflammation of bursas and tendons. Stabilized aFGF stimulates division in various cell types including fibroblasts, vascular and corneal endothelial cells, tympanic membrane cells and the like rendering stabilized aFGF and bFGF useful for vascular repair, the production of artificial vessels and typanic membrane repair. Stabilized aFGF of the present invention is also useful in promoting the healing and regeneration of cartilage and cartilageneous tissue. The stabilizers of the present invention are able to maintain aFGF in a biologically active state under adverse conditions such as increased temperature and oxidation.

The following examples illustrate the present invention without, however, limiting the same thereto.

EXAMPLE 1

Thermal Stability Of aFGF In The Presence Of Heparin

To examine the interactions between aFGF and heparin, a spectrophotometric turbidity assay was developed. This technique monitors the structural stability of aFGF by following the kinetics of temperature induced aggregation of unfolded protein by measurement of the degree of light scattering (turbidity) at 350 nm. The kinetics of protein aggregation were monitored by the degree of light scattering at 350 nm using a Perkin Elmer Lambda 6 UV-visible spectrophotometer equipped with a six-cuvette holder. Temperature was controlled by circulating a water/ethylene glycol solution through the cell holder. A PBS solution, 0.9 ml, (6 mM phosphate, 120 mM NaCl pH 7.2) was placed into a cuvette and incubated at the appropriate temperature within the spectrophotometer. Once equilibrated, 100 $\mu$l of a 1 mg/ml aFGF solution containing the appropriate amount of ligand was added to the cuvette and mixed manually by inversion. The change in optical density at 350 nm over time was continuously monitored. A dead time of 30s was present due to the mixing of the six samples in each experiment.

As shown in FIG. 1, aFGF undergoes rapid aggregation when heated at 55° C. Samples contained 100 $\mu$g/ml aFGF in a PBS buffer at pH 7.2 with the indicated ratio of heparin to aFGF (wt:wt). As the amount of heparin (average molecular weight of 16,000) added to aFGF is increased from 0.1 to 3X heparin (by weight), the stabilization of aFGF is dramatically enhanced with no aggregation observed after 25 minutes at 55° C. in the presence of a 3-fold excess of heparin.

Figure 2B:
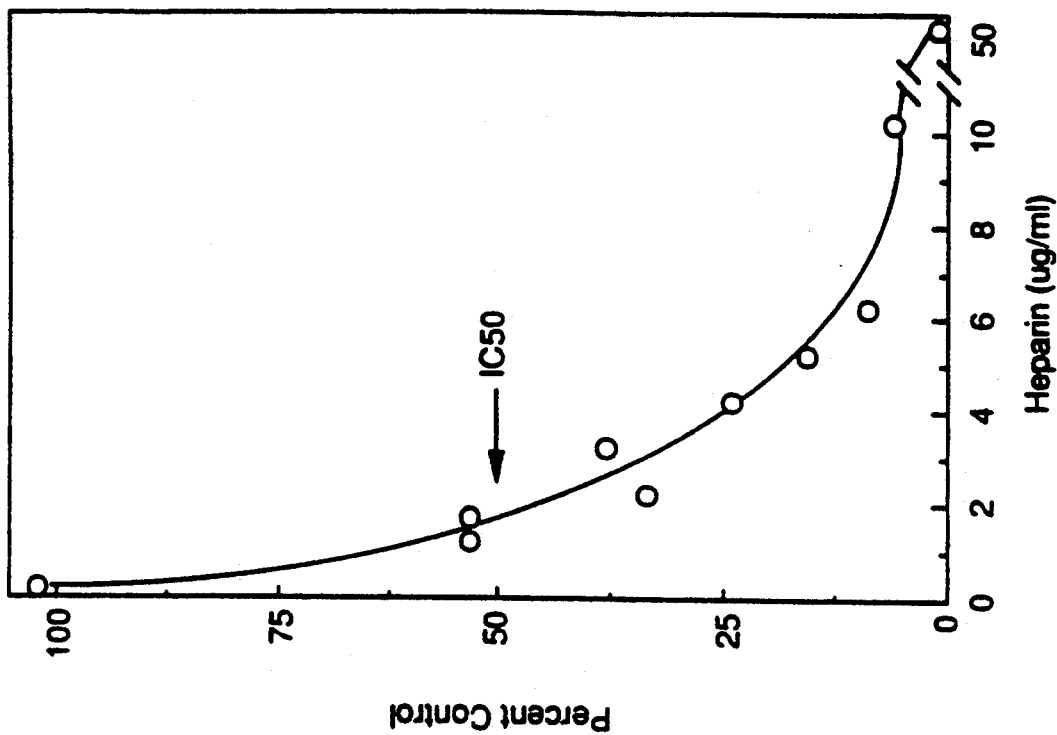
FIG. 2. Effect of heparin concentration on the heat-induced aggregation of acidic FGF at 40° C.
 (A) Time course of turbidity formation.
 (B) Effect of heparin on aFGF thermal stability at 40° C.
Figure 2A:
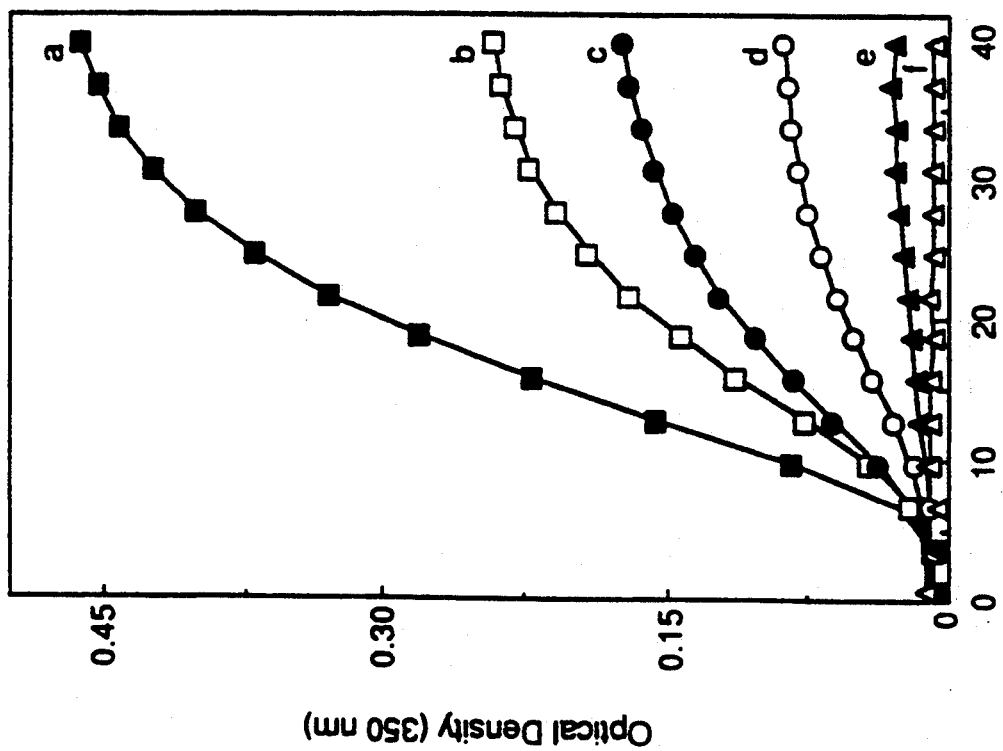

The rate of aFGF aggregation is strongly dependent on temperature. At lower temperatures, the time course of aFGF aggregation can be followed in the absence of heparin. For example, at 40° C. the rate of aFGF aggregation both with and without polyanions present can be measured as shown in FIG. 2A. Samples contained 100 $\mu$g/ml protein in a PBS buffer, pH 7.2 with (a) no heparin, (b) 1.5 $\mu$g/ml, (c) 3 $\mu$g/ml, (d) 5 $\mu$g/ml, (e) 10 $\mu$g/ml and (f) 50 $\mu$g/ml heparin. Only representative data points are shown for clarity. As expected, increasing amounts of heparin inhibit the rate of aFGF aggregation. Using the initial linear portion of the slope of turbidity vs. time plots as a measure of the rate of aggregation, the effect of polyanion concentration can be quantitatively characterized. The Y-axis represents the maximum rate of turbidity formation ($\Delta OD_{350}$ nm/min) normalized to sample (a) containing no heparin. The curve is drawn through data points for clarity only. The IC50 is the concentration of ligand at which the rate of aggregation is 50% of the control sample. Using this approach (FIG. 2B), no detectable aggregation of aFGF was observed until the concentration of heparin was approximately 10 $\mu$g/ml or less (1:10 weight ratio of heparin to aFGF).

Figure 3B:
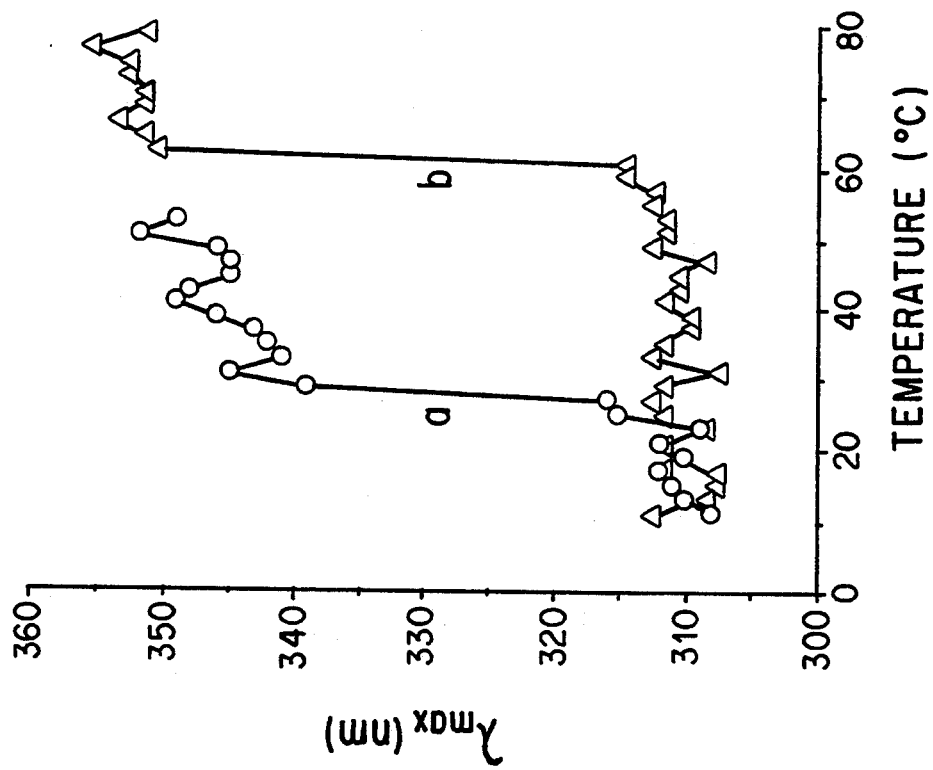
FIG. 3. Effect of heparin concentration on the thermal melting temperature ($T_m$) of aFGF as measured by fluorescence spectroscopy.
Figure 3A:
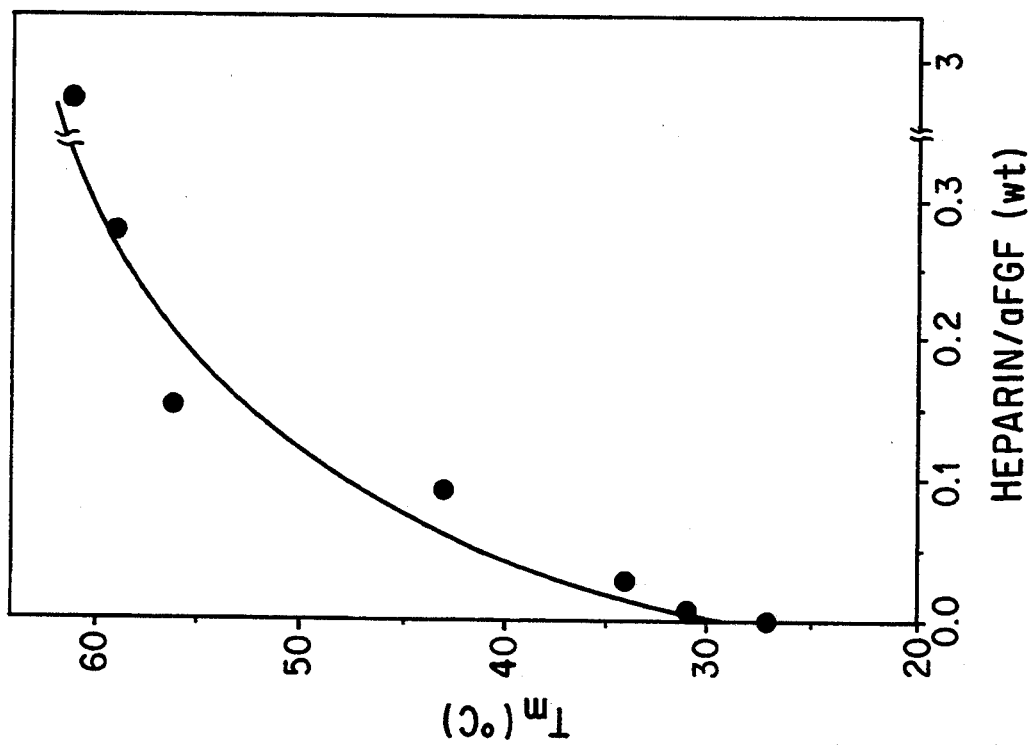

To more directly ascertain the effect of heparin on aFGF stability, the temperature-induced denaturation of aFGF as a function of heparin concentration was monitored by fluorescence spectroscopy. Fluorescence spectra were obtained with a Spex Fluorolog-2 spectrofluorometer using a 1 mm pathlength cuvette. Band passes from 1–2 nm were employed with sample absorptivities maintained below 0.1 at 280 nm. The temperature was controlled either manually or automatically as described above. Reproducibility of thermal denaturation temperatures ($T_m$) was $\pm 2°$ C. It should be noted that the fluorescence spectra of native aFGF ($T_m < 30°$ C.) does not change upon the addition of heparin (or any of the other anions used in this study). The effect of temperature on the fluorescence emission (280 nm excitation) of aFGF has been examined previously, and it has been shown that wavelength emission maximum shifts from 309 to 350 nm upon denaturation. A comparison of the thermal denaturation of aFGF with and without heparin is illustrated in the insert of FIG. 3. Experiments were carried out at 100 $\mu$g/ml protein (6.3 $\mu$M) in a PBS buffer at pH 7.2. Curve drawn through data points for clarity only. The insert displays a representative experiment in which the fluorescence wavelength maximum of acidic FGF is measured as a function of temperature; (a) buffer alone and (b) buffer containing 3X (wt) heparin. The effect of varying heparin concentrations on the thermal denaturation temperature ($T_m$) of aFGF is shown in FIG. 3. In the absence of heparin, aFGF denatures at 27° C. in a PBS buffer, pH 7.2. As the weight ratio of heparin to aFGF is increased from 1/100 to 1/3X, aFGF thermal stability is significantly enhanced with $T_m$ values increasing to 59° C. When excess heparin is added (3X by weight), the maximum stabilization of aFGF is at a $T_m$ of 61° C. The concentration of heparin necessary to obtain one-half the $T_m$ maximum is 0.1X (by weight).

Figure 4B:
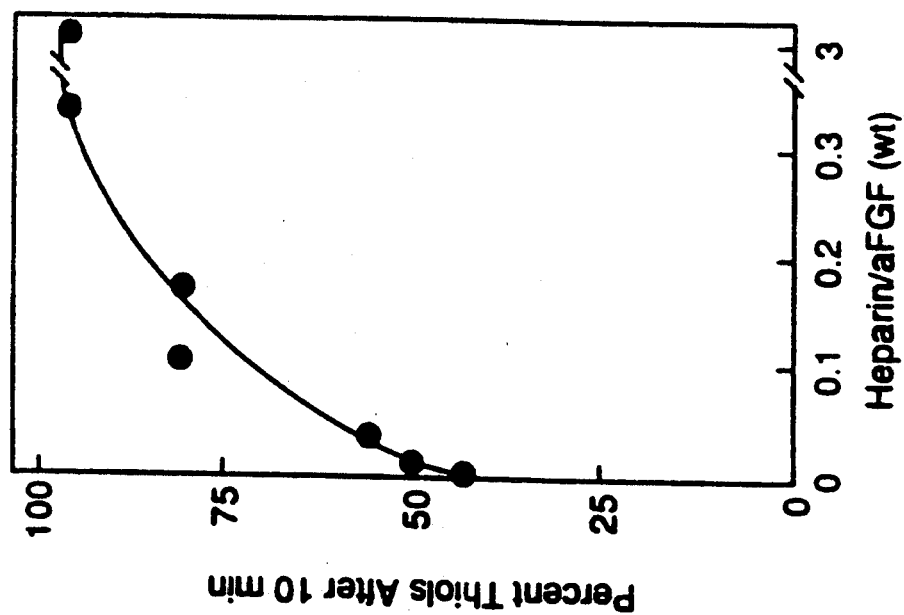
FIG. 4. Effect of heparin on the copper-catalyzed oxidation of aFGF.
 (A) The time course of aFGF thiol groups remaining in solution during incubation with cuptic chloride.
 (B) Effect of heparin concentration on the percentage of aFGF thiol groups remaining in solution after a 10-minute incubation with cuptic chloride.
Figure 4A:
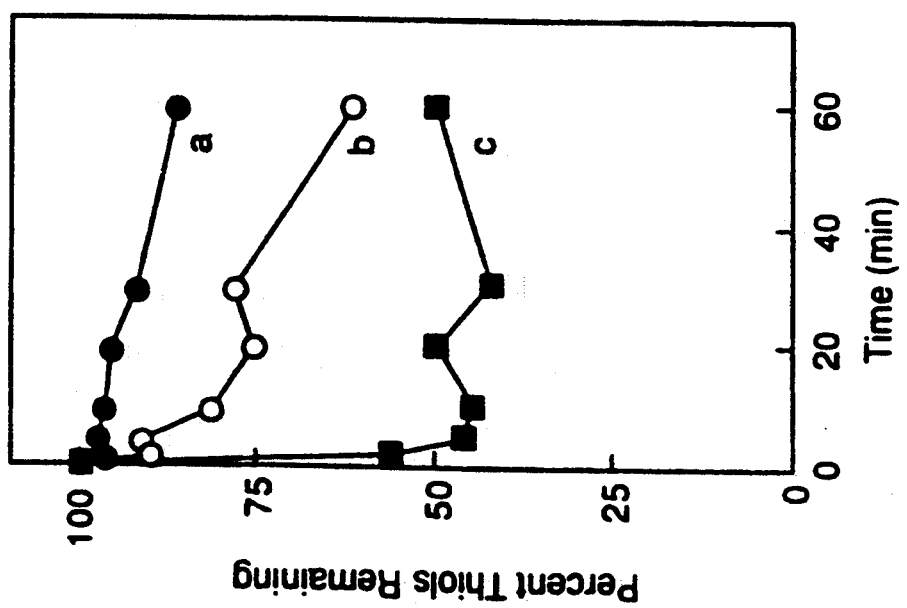

Acidic FGF contains three free cysteine residues at positions 47, 83 and 117 in the polypeptide chain. Site-directed mutagenesis experiments have shown that routants in which serine is substituted for cysteine are more stable and less heparin dependent than wild-type protein, Linemeyer, et al., Growth Factors 3:287-298 (1990). It has also been shown that the copper catalyzed oxidative formation of a disulfide bond in the wild-type aFGF inactivates the protein in an in vitro mitogenic assay, Ortega et al., J. Biol. Chem. 266:5842-5846 (1991). Therefore, it was of interest to determine the extent to which heparin can stabilize aFGF against inactivation by oxidation. As shown in FIG. 4A, 50-60% of the aFGF's thiol groups are oxidized within several minutes followed by a slower reaction (in which after 6 hours 70-75% of total thiol groups reacted). Samples contained 80 μg/ml aFGF with (a) 3X heparin by weight, (b) 0.1X heparin by weight and (c) buffer alone. As heparin was introduced and its concentration increased, the rate of copper-catalyzed oxidation decreased. For example, after 20 minutes, greater than 95% of the cysteine residues of aFGF are protected from oxidation with 3X heparin. FIG. 4B illustrates the fraction of remaining reactive thiol groups after a 10-minute incubation with cupric chloride as a function of heparin concentration. The data show a heparin concentration dependence similar to that seen in the thermal denaturation experiments with stabilization essentially complete at ⅓ weight levels of heparin.

Some aggregation of aFGF occurs under the conditions of these experiments presumably due to at least partial intermolecular disulfide formation. Thus, these measurements could simply be a measurement of the loss of solubility induced by copper association with aFGF. Several experiments, however, argue against this possibility. First, previous work has shown that at dilute protein concentration, copper does indeed catalyze oxidation of thiol groups of aFGF, Ortega et al., J. Biol. Chem. 266:5842-5846 (199 1). Second, as a control experiment, the copper-catalyzed oxidation of aFGF was carded out in a buffer containing 6 M GuHCl. Under these denaturing conditions, nearly 100% of the thiol groups in solution were lost after 10 minutes without visible aggregation. Finally, when these denaturing experiments (5 μM aFGF) were carded out with lower concentrations of $CuCl_2$ (1-20 μM), oxidation still proceeded although at a slower rate (10% loss after 10 minutes with 1 μM $CuCl_2$), indicating that oxidation by copper is catalytic, not stoichiometric. Regardless of the precise mechanism, copper addition is a distinct mechanism of inactivation compared to thermal stress.

EXAMPLE 2

Molecular Weight Requirements For aFGF Heparin-Stabilizers

Figure 5:
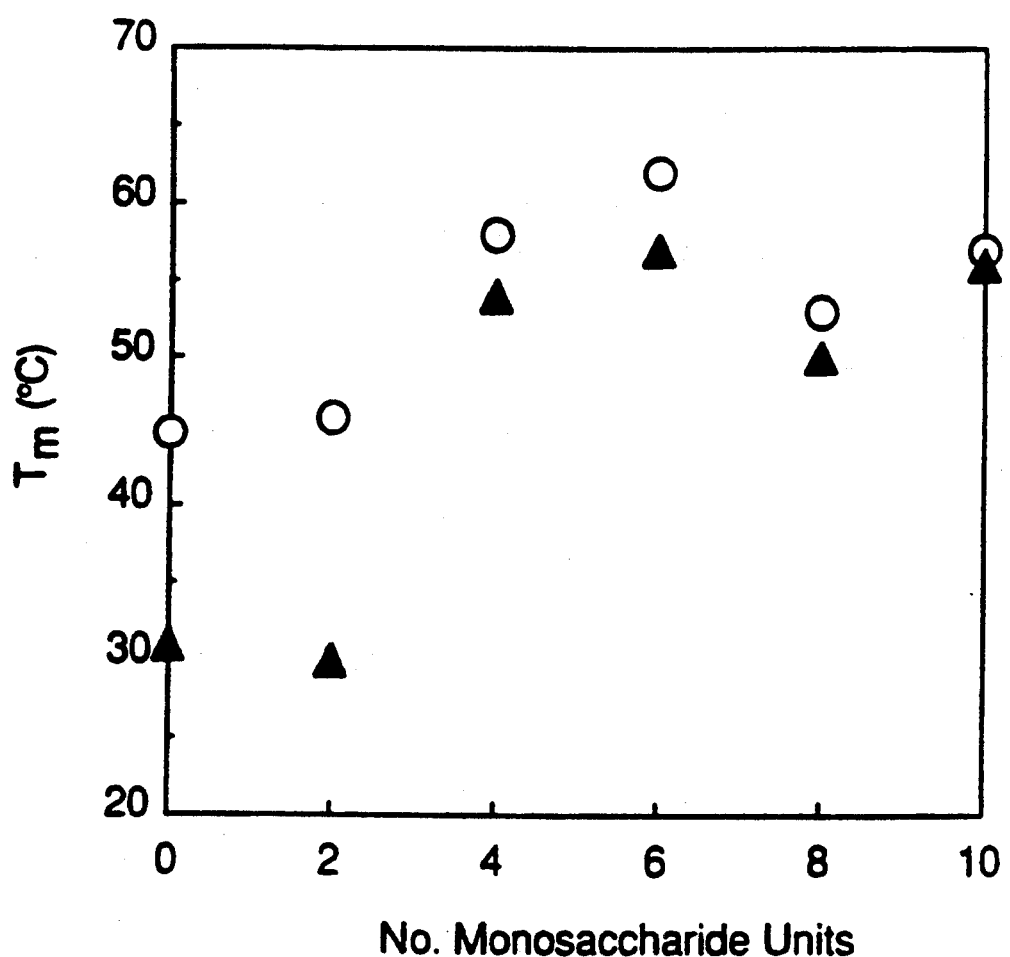
FIG. 5. Effect of the size (in monomeric hexose units) of well-defined heparin fragments on the thermal melting temperature of aFGF as measured by fluorescence spectroscopy and circular dichroism.

Studies of the stabilization of aFGF by heparin are difficult to interpret because of the inherent heterogeneity of heparin preparations, Lane and Lindahl, Eds. Heparin, Chemical and Biological Properties, Clinical Applications, Edward Arnold, London (1989); Jackson, et al., Physiol. Rev. 71: 481-539 (1991). In order to better understand the polyanionic stabilization of aFGF, a series of well-defined fragments of heparin were examined for their ability to stabilize aFGF against thermal denaturation. These enzymatically prepared and purified fragments varied in size from a disaccharide to a decasaccharide. Each fragment was incubated with aFGF at a 1:1 weight ratio in a PBS buffer. The sample was then stressed by temperature and structural changes in aFGF were monitored by both circular dichroism and fluorescence spectroscopy. The results of these experiments are summarized in FIG. 5 (fluorescence spectroscopy [triangle] and circular dichroism [circle]). All samples contained 100 μg/ml aFGF (6.3 μM)in a PBS buffer (pH 7.2) with 100 μg/ml of each heparin fragment. Although the disaccharide did not influence the $T_m$ of aFGF, higher molecular weight fragments (tetramer, hexamer, octamer and decamer) all stabilized aFGF to approximately the same extent as heparin itself. Thus, the tetrasaccharide is the smallest unit of heparin capable of stabilizing aFGF against thermal denaturation.

Since these fragments of heparin have a well-defined molecular weight, the molar ratio of aFGF to ligand during these thermal denaturation experiments can be calculated. The $T_m$ of aFGF as a function of the molar concentration of the hexasaccharide was measured by fluorescence spectroscopy. Fluorescence spectra were obtained with a Spex Fluorolog-2 spectrofluorometer using a 1mm pathlength cuvette. Band passes from 1-2 nm were employed with sample absorptivities maintained below 0.1 at 280 nm. The temperature was controlled either manually or automatically as described above. Reproducibility of thermal denaturation temperatures ($T_m$) was ±2° C. The stabilization of aFGF increases rapidly between 0 and 1 moles ligand/mole aFGF and then slowly plateaus in the presence of excess ligand. The 50% stabilization concentration (the value at one-half of the total $T_m$ shift) occurs at approximately 0.5 moles heparin hexasaccharide per mole aFGF.

Chemically modified heparins, with varying levels of sulfation, were used to investigate the effect of heparin sulfation on human aFGF stability. When the sulfur content of heparin was raised from 1.5% to 4.5-7% to >8% to 13.5% the $T_m$ (fluorescence) of aFGF increased form 27° C. to 33° C. to 39° C. to 56° C. (at ⅓x heparin by weight) and from 28° C. to 49° C. to 49° C. to 62° C. (at 3x heparin by weight). Clearly, increasing the sulfation of heparin enhances the stabilization of human aFGF.

EXAMPLE 3

Thermal Stability Of aFGF In The Presence Of Polyanions

Figure 6:
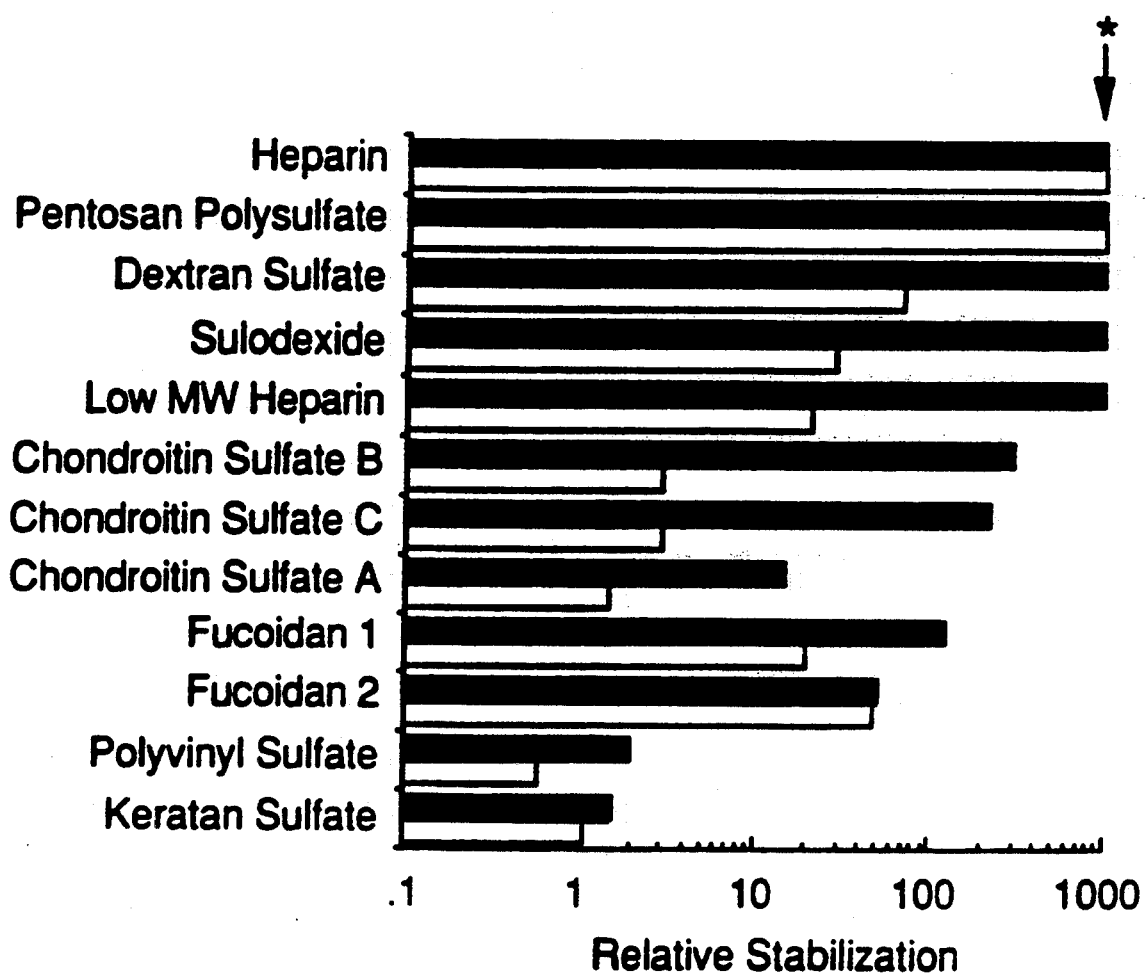
FIG. 6. Stabilization of aFGF against heat-induced aggregation at 40° C. by various heparin-like molecules.
Figure 7:
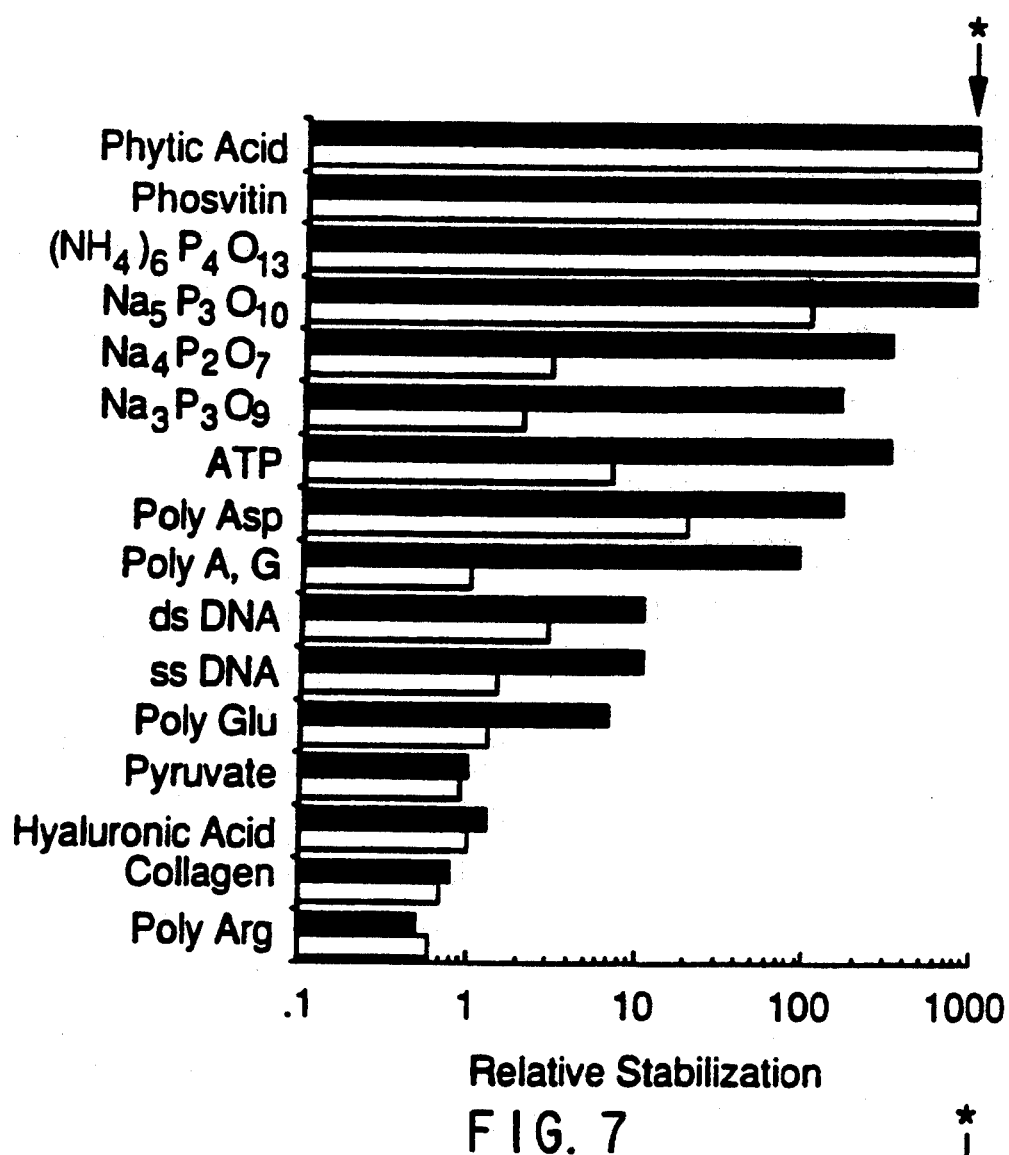
FIG. 7. Stabilization of aFGF against heat-induced aggregation at 40° C. by various polyanions.

To further explore the structural requirements for the stabilization of aFGF by ligands, various polyanionic and sulfated molecules were examined. Compounds were initially screened by the turbidity method described above. Using the criteria of the initial rate of aggregation (AOD$_{350}$ $_{nm}$/min) and extent of aggregation (OD$_{350}$ $_{nm}$ after 15 minutes), the ability of a wide variety of agents to stabilize aFGF was examined. The results are shown in FIGS. 6 and 7. (*)indicates no aggregation was observed during the time course of the experiment. The compounds have been divided into 3 categories: heparin-like molecules, other polyanions, and small sulfated compounds. All of the sulfated polysaccharides and polymers stabilized aFGF although the extent of this stabilization varies significantly (FIG. 6). The extent of aggregation (ΔOD$_{350}$ $_{nm}$ at 15 minutes) was measured for aFGF in the presence of 0.5X (closed box) and 10X (open box) ligand (by weight) and then normalized to acidic FGF samples in buffer alone. Experimental conditions are described in FIG. 2. For example, a 10X concentration (by weight) of chondroitin sulfate A, B or C significantly slows down the rate and extent of aggregation while 0.5X has only a slight effect. Sulfated polysaccharides such as low MW heparin, sulodexide, dextran sulfate, fucoidan, and pentosan polysulfate all dramatically stabilize aFGF from heat-induced aggregation. In fact, with many of these compounds, no aggregation was detected within the time course of the experiment. Other sulfated polymers such as polyvinyl sulfate and keratan sulfate are much less effective.

Figure 8:
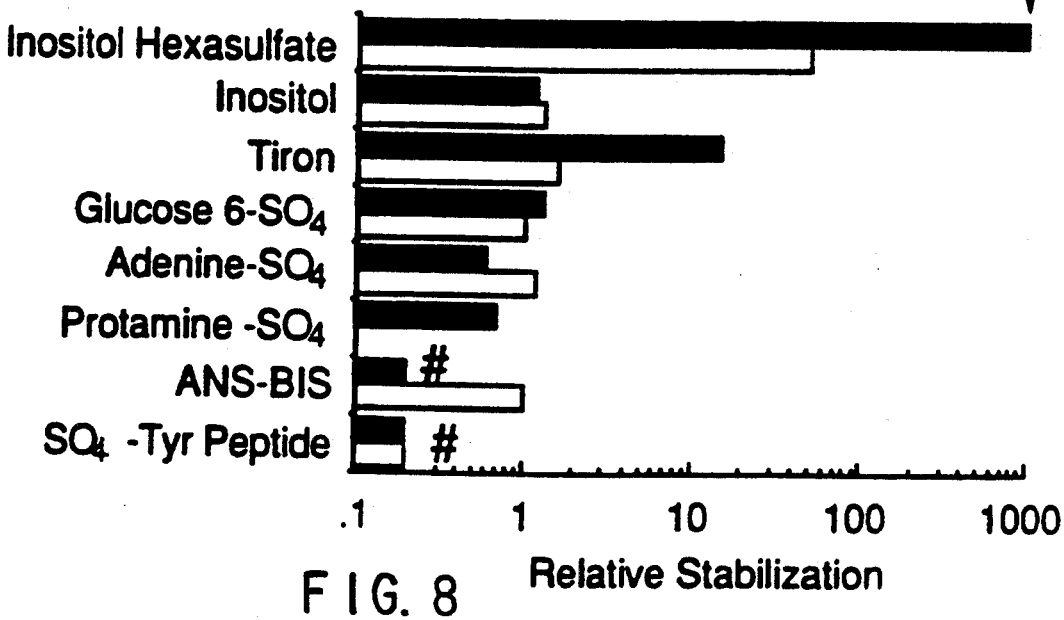
FIG. 8. Stabilization of aFGF against heat-induced aggregation at 40° C. by various small sulfated molecules.
Figure 9D:
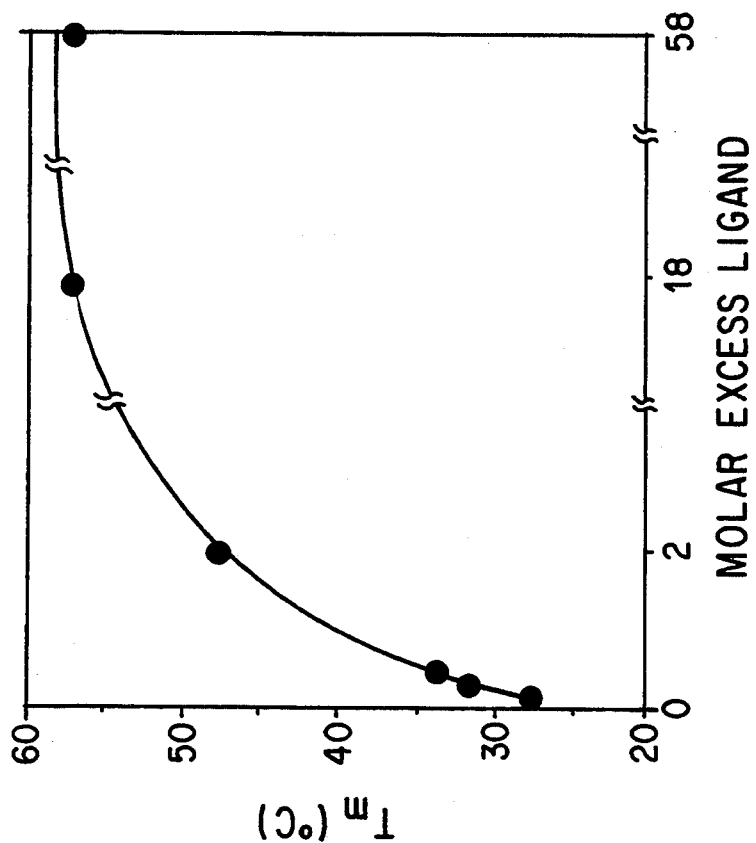
FIG. 9. Effect of the molar ratio of various ligands to aFGF on the thermal denaturation of acidic FGF as measured by fluorescence spectroscopy is shown for inositol hexasulfate in panel A; tetrapolyphosphate in panel B; inositol hexaphosphate in panel C; and sulfated beta-cyclodextrin in panel D.
Figure 9C:
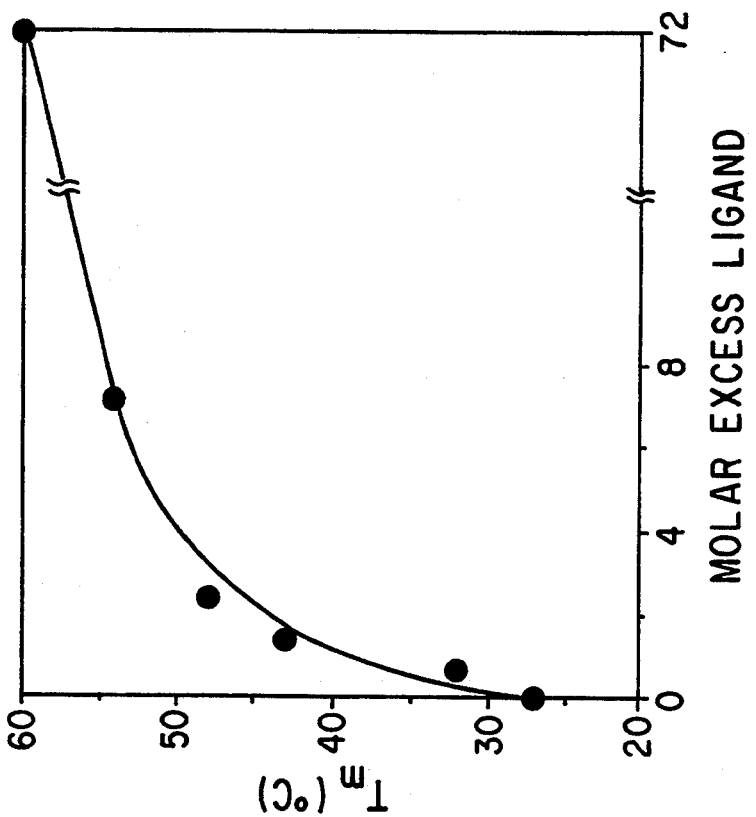

FIG. 7 shows that negatively charged species as varied as ATP, inorganic phosphates, phosphorylated inositols and polyamino acids (poly-Asp and poly-Glu)can all significantly enhance the thermal stability of aFGF. In contrast, positively charged polymers such as poly-Arg alestabilize aFGF. Small sulfated molecules such as inositol hexasulfate also stabilize aFGF against heat-induced aggregation. Other small sulfated compounds, however, such as a sulfated tyrosine peptide and adenine sulfate actually alestabilize the growth factor (see FIG. 8, [*] indicates no aggregation and [#] indicates very rapid aggregation during the time course of the experiment.

The effect of ligand concentration on the inhibition of aggregation was examined in more detail for some representative compounds. The results of some of these experiments in terms of the concentration which produced 50% inhibition (see FIG. 2) are summarized in the following table.

TABLE 1

Inhibition of heat induced aggregation of acidic FGF in the presence of various amounts of stabilizing ligands at 40° C.

| | Approx. MW | IC50* µg/ml | Approx. Molar Ratio |
|---|---|---|---|
| Heparin | 16,000 | 2 | 0.03 |
| Low MW heparin | 5,000 | 3 | 0.10 |
| Phosvitin | 40,000 | 3 | 0.02 |
| Dextran sulfate | 8,000 | 3 | 0.06 |
| Fucoidin | N/A | 6 | — |
| Chondroitin Sulfate B | N/A | 50 | — |
| Inositol hexasulfate | 890 | 3 | 0.6 |
| Tetrapolyphosphate | 440 | 3 | 1.2 |
| Ammonium sulfate | 132 | 70 | 80 |
| Lactobionic acid | 358 | 180 | 80 |
| | | IC50* (µM) | |
| Phosphate buffer | 142 | 6000 | 1000 |
| Nucleotides | | | |
| ADP | 427 | 200 | 33 |

TABLE 1-continued

Inhibition of heat induced aggregation of acidic FGF in the presence of various amounts of stabilizing ligands at 40° C.

| | Approx. MW | | Approx. Molar Ratio |
|---|---|---|---|
| ATP | 551 | 30 | 5 |
| AT4P | 587 | 10 | 1.6 |
| Diadenosine | | | |
| Nucleotides | | | |
| Ap3A | 756 | 250 | 42 |
| Ap4A | 836 | 30 | 5 |
| Ap5A | 916 | 10 | 1.6 |
| Ap6A | 996 | 3 | 0.5 |

*IC50 is the concentration of ligand at which the rate of heat-induced aggregation (ΔOD$_{350}$/min) of aFGF is 50% of the sample without ligand. Experimental conditions are described in FIG. 2.

The concentration dependencies seem to fall into three categories. Polymers such as heparin, dextran sulfate and phosvitin require molar ratios of polyanion to aFGF substantially below one, suggesting binding of multiple growth factor molecules to a single polymer. Small, multiply negatively charged compounds such as tetrapolyphosphate and inositol hexasulfate appear to interact with aFGF with high affinity with only one or a few ligands per aFGF molecule providing the observed stabilization. In contrast, small singly charged molecules such as ammonium sulfate and lactobionic add (non-sulfated) appear to bind only weakly to aFGF as reflected by the large number of such molecules (about 80) necessary to produce maximal stabilization.

Analogous to the heparin experiments illustrated in Example 1 (FIG. 3), aFGF thermal stability was monitored by fluorescence spectroscopy as a function of concentration for several other of the polyanions. Results of four of the more effective nonpolymeric compounds, inositol hexasulfate, tetrapolyphosphate, phytic add and sulfated β-cyclodextrin are shown in FIG. 9A-D [(A)inositol hexasulfate, (B) tetrapolyphosphate, (C)inositol hexaphosphate and (D) sulfated β-cydodextrin]. All samples contained 100 µg/ml of aFGF (6.3 µM) in a PBS buffer at pH 7.2. In each case, as the molar concentration of ligand was increased a dramatic stabilization of aFGF was observed as monitored by shifts in T$_m$ values. In each case, a clear saturation effect was observed. The values of the T$_m$ maximum vary from 50° C. (tetrapolyphosphate) to 53° C. (inositol hexasulfate) to 56° C. (sulfated β-cyclodextrin) to 60° C. (phytic add). These values should be compared to those observed with heparin (T$_m$ maximum of 61° C.). Since these low molecular weight ligands have well defined molecular weights, the molar excess of ligand to aFGF required for 50% stabilization could be determined as approximately 6, 3.5, 1.5 and 2, respectively.

Figure 10:
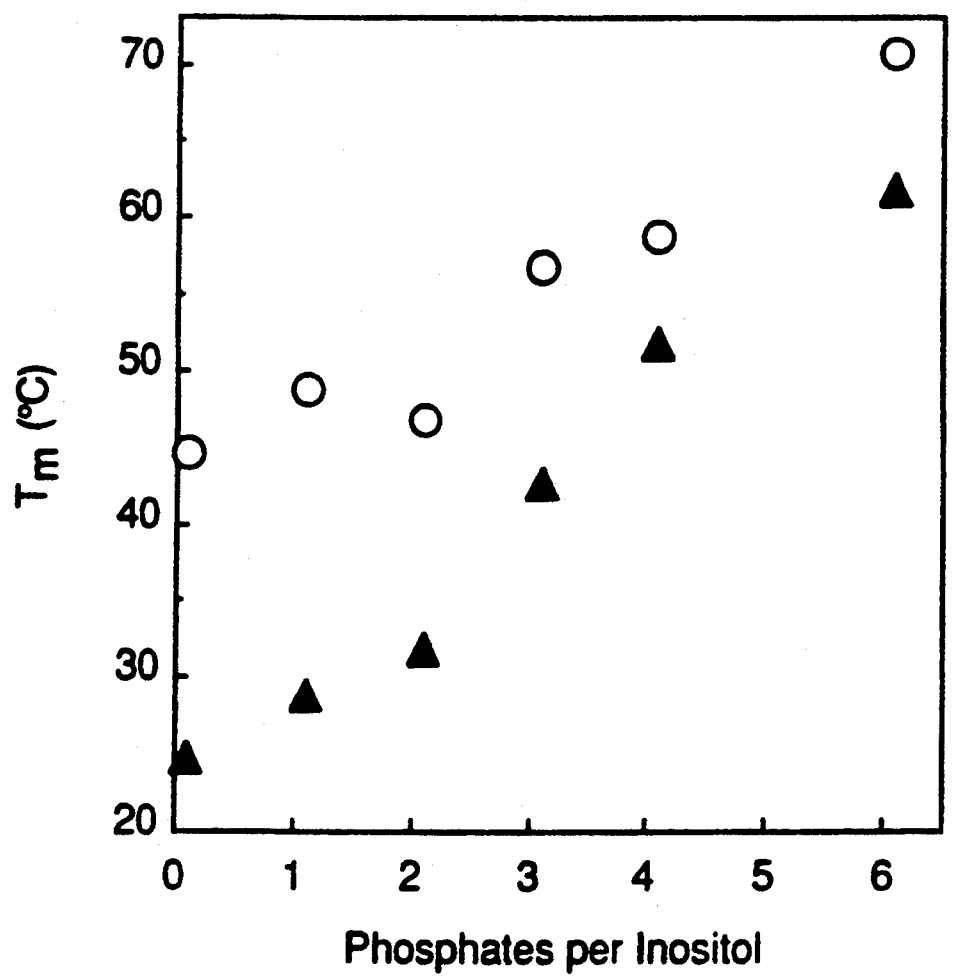
FIG. 10. Thermal denaturation of aFGF as a function of the number of phosphate groups on the ligand inositol as measured by fluorescence spectroscopy and circular dichroism.

One class of these compounds, the phosphorylated inositols, was used to investigate the effect of varying the charge on a stabilizing ligand. The thermal stability of aFGF was again measured by T$_m$ values as monitored by both fluorescence spectroscopic and circular dichroism measurements. As the number of phosphate groups on inositol was varied from zero to six, the thermal denaturation temperature of aFGF steadily increased (FIG. 10). The closed triangle represents fluorescence spectroscopy while the open circle represents circular dichroism. Samples contained 100 µg/ml addle FGF (6.3 µM) in a PBS buffer pH 7.2 with 300 µg/ml of each inositol derivative. The most profound effect appears to occur once the number of phosphate groups on inositol exceeds two.

Similar experiments were also conducted with β-cyclodextrins in which the extent of sulfation on the ligand was varied. When the sulfur content of β-cyclodextrin was raised from zero to 8% to 16% (i.e., approximately zero, one and two sulfate groups per monomer), the ligands (3X by weight) differed in their ability to stabilize aFGF ($T_m$ values of 46° C., 48° C. and 65° C., respectively, as measured by circular dichroism). By comparison, the $T_m$ of aFGF is 45° C. in buffer alone and 64° C. in the presence of 3X (by weight) heparin as measured by CD (see Table II). In contrast, propyl-hydroxy-β- cyclodextrin did not stabilize acidic FGF ($T_m$ 47° C.). Similar results (stabilization of aFGF at high sulfate content) were seen with a series of sulfated γ-cyclodextrins.

The maximum $T_m$ values induced by 12 different ligands as determined by circular dichroism measurements at 228 nm are summarized in the first column of Table II. All of these ligands stabilize aFGF by 15°-25° C. in a manner similar to that originally observed with heparin. The X-ray crystallographic determination of the three-dimensional structure of aFGF found that a heavy atom derivatizing agent $(IrCl_6)^{-3}$ is bound by several basic residues that are presumed to be near the heparin binding site, Zhu, et al., Salenee 251: 90–93 (1991). Furthermore, sulfate unions are found near analogous residues in the crystal structure of basic FGF, Eriksson et al., Proc. Natl. Acad. Sd. USA 88:3441–3445 (1991); Zhang et al., Proc. Natl. Acad. Sci. USA 88:3446–3450 (1991). Consequently, it seemed important to examine the ability of these ligands to stabilize aFGF during thermal denaturation as monitored by both fluorescence and circular dichroism. The $T_m$ value of aFGF increased from 27° C. to 43° C. (fluorescence) and 45° C. to 51° C. (CD) when a 100 molar excess (3X by weight) of $(IrCl_6)^{-3}$ was present. Similarly, sulfate union (120 mM) produced a species that was even more dramatically stabilized, melting at 57° C. (CD).

Similar protection against oxidation experiments were carried out with other negatively charged compounds with an excess of ligand (3X by weight except for sodium sulfate at 120 mM and tetrapolyphosphate at 10 mM) added to aFGF before copper catalyzed oxidation. As shown in the second column of Table 2, all of these agents at least partially protect the cysteine residues of aFGF from oxidation.

The extent of protection, however, varies from less than 3% to over 25% of free thiols lost after a 10-minute incubation compared to 60% of thiols lost in the absence of polyanions. Some of these compounds such as tetrapolyphosphate and phytic acid are well known metal chelators, so part of their protective effect against oxidation could be due to chelation of divalent metal cations in addition to their direct interaction with the protein itself. An interesting comparison can be made between inositol hexasulfate and inositol hexaphosphate (Table 2). Both ligands stabilize aFGF against thermal denaturation (CD $T_m$ values of 66° C. and 70° C., respectively). However, inositol hexaphosphate (phytic acid)is more potent in protecting the growth factor from oxidation (<3% vs. 22% of thiol groups lost in 10 minutes). Like heparin, the concentration of each of the ligands required for maximum protection against oxidation was similar to the amount needed to stabilize aFGF against thermal denaturation.

TABLE 2

Biophysical and biochemical characterization of aFGF with stabilizing ligands.

| Additive | $T_m^{(a)}$ | Cu Oxidation[b] (% SH Lost in 10 Mins) | Anticoagulant Activity of Ligand[c] (% Heparin by Wt) | Bioactivity[d] |
|---|---|---|---|---|
| Buffer alone | 45 | 60% | 0 | <0.25 |
| Sodium Sulfate MW 142 | 57 | 25% | N.P. | 0* |
| Tetrapolyphosphate MW 440 | 66 | <3% | + | <0.25 |
| Inositol hexaphosphate MW 660 | 70 | <3% | + | <0.6 |
| Inositol hexasulfate MW 890 | 66 | 22% | + | 2.3 |
| Sucrose octasulfate MW 1300 | 65 | N.P. | N.P. | 2.5 |
| Sulfated lactobionic acid amide MW 2600 | 62 | N.P. | N.P. | 4.2 |
| Sulfated β-cyclodextrin MW 2,500 | 65 | <3% | ++ | 3.7 |
| Sulfated γ-cyclodextrin MW 3,000 | 70 | 5% | ++ | N.P. |
| Pentosan polyphosphate MW 5,000 | 60 | 6% | N.P.m | N.P. |
| Low MW heparin MW 5,000 | 66 | <3% | ++ | 4.0 |
| Dextran sulfate MW 8,000 | 62 | 7% | ++ | 5.0 |
| Heparin MW 16,000 | 64 | <3% | +++ | 4.2 |

[a]Thermal melting temperatures were measured by circular dichroism. Samples contained 100 mg/ml aFGF in PBS buffer pH 7.2 with excess ligand (1–3× by weight except for 120 mM sodium sulfate and 10 mM tetrapolyphosphate.
[b]Percentage of aFGF thiols remaining in solution after 10 min incubation with cupric chloride. Experimental conditions are described in FIG. 10. All samples contained ligand at 3× (by weight) except sodium sulfate (120 mM) and tetrapolyphosphate (10 mM).
[c]Anticoagulant activity is expressed as a fraction of activity observed with an equal weight of heparin (+ less than 1/10; ++ 1/10 to ½; +++ heparin). No aFGF is present during these measurements.
[d]Mitogenic activity of aFGF was measured in the presence of ligand indicated in the complete absence of heparin.
<indicates mitogenic response did not plateau and
*indicates cell death observed during assay.
N.P. indicates experiment not performed.

EXAMPLE 4

Anticoagulant Properties Of Heparin Substitutes And Bioreactivity of aFGF

The anticoagulant properties of heparin are well established, so it was of interest to determine the relative anticoagulant properties of the ligands of this study. The anticoagulant effect of these molecules was measured using a dotting time assay (see methods). Clotting times were monitored by either a one-stage plasma prothrombin time assay (PT assay) or an activated partial thromboplastin time assay (aPTT) using an automated optical detection system (coag-a-Mate*-XC) by General Diagnostics. Clotting times were measured in the presence of varying amounts of heparin (0–50 μg heparin/ml plasma) to generate a standard curve and dotting times of other compounds (at equal wt. amounts) were obtained relative to these standardized values. The ability of these molecules to lengthen clotting times was roughly proportional to their molecular weight with values from ½ to less than 1/10 of heparin.

Biological activity of the formulation of the instant invention was determined by a modification of the fibroblast mitogenic assay as described by Linemeyer et al. in European Patent Application, Publication No. 259,953. BALB/c 3T3 A31 fibroblasts (American Type Culture Collection) were plated at $3 \times 10^5$ cells per 32 cm$^2$ well in culture media containing about 10% heat-inactivated calf serum and incubated in 7% $CO_2$ (pH 7.35±0.05). The cells become fully quiescent by replacing the media with serum free media at 6, 24 hours and 48 hours later. At 53 hours after plating samples of the various formulations were added and 0.12 μg of dexamethasone was added, at 65 hours each well was supplemented with 0.4 μCi of [methyl-$^3$H]-thymidine (20 Ci/mmole, Dupont) and 0.6 μg of unlabeled thymidine (Sigma), and at 80 hours the cells were processed for determination of radiolabel incorporation into DNA. Each dose-response point is the average of at least quadruplicate determinations. Other cell types such vascular endothelial cells and corneal endothelial cells can be employed to determine in vitro mitogenidty. The procedures are described in detail by Thomas et al., Proc. Natl. Acad. Sci. USA 82:6409–6431 (1985).

The mitogenic activity of aFGF combined with the heparin substitutes listed in Table 2 was examined. As summarized in Table 2, various polyanions can be successfully substituted for heparin. These data show that the in vitro mitogenic activity of aFGF is not specifically dependent on heparin itself, but rather on the presence of a stabilizing ligand. There does, however, seem to be a molecular weight or sulfation minimum for this effect since aFGF did not show any appreciable mitogenic activity in the presence of the smaller ligands examined (tetrapolyphosphate and phytic acid). Tetrapolyphosphate, and presumably all ligands, showed activity when assayed in the presence of heparin. No direct correlation is seen between the anticoagulant activity of polyanions and their ability to stabilize and activate aFGF.

EXAMPLE 5

Evaluation Of Stability Of aFGF Formulations In Polyethylene Unit Dose Tubes Acidic fibroblast growth factor was prepared and purified as described above. Sterile aFGF stabilizers were added at the desired concentration to aFGF. This solution was aseptically mixed with a solution of hydroxyethyl cellulose (HEC) and subdivided into previously sterilized 1 ml polyethylene tubes. The tubes were heat sealed and stored at either 5° or 30° C. for various lengths of time.

A formulation containing human aFGF at 100 μg/ml, 10 mM tetrapolyphosphate, 1% HEC in physiological saline was stored in low density polyethylene tubes for various lengths of times at 30° C. This formulation shows no loss in protein mass or biological activity after storage for 3 months.

A formulation containing aFGF at 50 μg/ml combined with sulfated β-cydodextfin (3X by weight), 1% HEC and 1 mM EDTA in phosphate buffered saline (pH about 7.2) was stored as described above. This formulation was stable for at least 6 months at both 30° C. and 4° C. (there was no loss of protein mass or biological activity). This formulation also showed biological efficacy in the in vivo wound healing model (Example 6).

A formulation containing aFGF at 250 μg/ml combined with 5X inositol hexasulfate (by weight), 1% HEC, 1 mM EDTA in PBS was stable for 1 month at 30° C. and for 2 months at 4° C. This formulation was also effective in enhancing wound healing (Example 6).

EXAMPLE 6

Determination Of In Vivo Bioactivity Of aFGF Formulation Containing Stabilizers Human aFGF as described above was combined with various stabilizers to evaluate wound healing activity of the stabilized aFGF. The in vivo animal wound healing model employs genetically diabetic C57GBL/Ks-db+/db+female mice (Jackson Laboratory). The assay follows that described by Marsella et. al., Wounds: A Compendium of Clinical Research and Practice, 2, (4) July/August 1990, p. 135–147 except that a single 2 cm$^2$ full thickness wound is used instead of the two 6 mm biopsy wounds described by Marsella. Another difference is that the wounds are covered with a polyurethane dressing. Acidic FGF is applied to wounds on days 0, 3 and 7. Matching placebo formulations are used in a second group of animals. Dressings are changed every three to four days, at which time wound perimeters are traced for assessment of healing. Comparison of healing rate vs. a placebo control is made and evaluated for statistical significance at the 90% healed stage. The wound healing capability of various formulations of stabilized aFGF are shown below. The aFGF-nonheparin formulations as shown in Example 5 while the aFGF-heparin formulation contains 50 μg/ml aFGF, sterile bovine lung heparin (Hepar Industries) 3X (by weight), 1% HEC in PBS. Both inositol hexasulfate and sulfated β-cyclodextrin are as efficacious as heparin in stimulating, presumably through stabilization) the wound healing activity of aFGF as manifested in the shortening of healing times.

TABLE 3

| Treatment | HT50 (Days) | HT70 (Days) | HT90 (Days) | HT100 (Days) |
|---|---|---|---|---|
| DB/DB Mouse Wound Healing Estimated Treatment Group Median | | | | |
| aFGF + Hep. | 8.49 | 10.82 | 13.76 | 24.00 |
| aFGF + Inos. | 8.07 | 10.61 | 14.19 | 21.00 |
| aFGF + Sul. β | 8.36 | 10.32 | 14.36 | 22.50 |
| Plac. + Hep. | 8.88 | 11.75 | 16.38 | 24.00 |
| Plac. + Inos. | 9.16 | 12.76 | 16.22 | 24.00 |
| Plac. + Sul. β | 8.78 | 11.39 | 15.61 | 24.00 |
| P-Values (2-sided) for Pairwise Comparisons aFGF vs. Placebo | | | | |
| Heparin | 0.417 | 0.128 | 0.068 | 0.079 |
| Inositol | 0.002* | <0.001* | 0.094 | 0.283 |
| Sul. β | 0.055 | 0.028 | 0.061 | 0.203 |

Hep. = heparin,
Inos. = inositol hexasulfate,
Sul. β = sulfated β-cyclodextrin,
Plac. = placebo and
* = two treatments were statistically significantly different ($P \leq 0.05$).

What is claimed is:

1. A stable aqueous medicinal composition comprising acidic fibroblast growth factor combined with a stabilizing amount of a compound selected from the group consisting of ATP, AT4P, Ap$_3$A, Ap$_4$A, Ap$_5$A and Ap$_6$A said compound stabilizing acidic fibroblast growth factor against loss of biological activity.

* * * * *